United States Patent [19]

Olds et al.

[11] Patent Number: 5,295,360
[45] Date of Patent: Mar. 22, 1994

[54] APPARATUS FOR IDENTIFYING AND DISTINGUISHING DIFFERENT REFRIGERANTS

[75] Inventors: Daniel L. Olds; Sandra Snyder, both of Bryan, Ohio

[73] Assignee: SPX Corporation, Muskegon, Mich.

[21] Appl. No.: 47,263

[22] Filed: Apr. 12, 1993

[51] Int. Cl.$^5$ ............................................. G01N 25/00
[52] U.S. Cl. ...................................... 62/127; 62/292; 73/25.03
[58] Field of Search ................. 62/125, 126, 127, 129, 62/149, 292; 422/83; 73/25.01, 25.03, 61.76, 61.46; 374/44

[56] References Cited

U.S. PATENT DOCUMENTS

| | | | |
|---|---|---|---|
| 4,768,347 | 9/1988 | Manz et al. | 62/149 |
| 4,805,416 | 2/1989 | Manz et al. | 62/292 |
| 4,878,356 | 11/1989 | Punches et al. | 62/149 |
| 4,939,905 | 7/1990 | Manz | 62/77 |
| 4,970,891 | 11/1990 | Blevins et al. | 73/25.03 X |
| 5,158,747 | 10/1992 | Manz et al. | 422/98 |
| 5,237,873 | 8/1993 | Eichenlaub | 62/127 X |

*Primary Examiner*—Harry B. Tanner
*Attorney, Agent, or Firm*—Barnes, Kisselle, Raisch, Choate, Whittemore & Hulbert

[57] ABSTRACT

Apparatus for identifying and distinguishing between at least two types of refrigerant that includes a fixed volume for containing a refrigerant sample at controlled vapor pressure. A thermistor provides a first electrical signal as a function of the combined effect of thermal conductivity and temperature of a refrigerant sample in the sample-containing volume, and a temperature sensor provides a second electrical signal as a function of temperature of the refrigerant vapor in the sample-containing volume essentially independent of thermal conductivity thereof. Associated electronics determines type of refrigerant in the sample-containing volume as a function of the first and second electrical signals, and thus as a function of thermal conductivity of the refrigerant sample independent of sample temperature. Since thermal conductivity of refrigerants at a given temperature and pressure varies for different refrigerant types, refrigerant type can be determined and displayed to an operator.

13 Claims, 2 Drawing Sheets

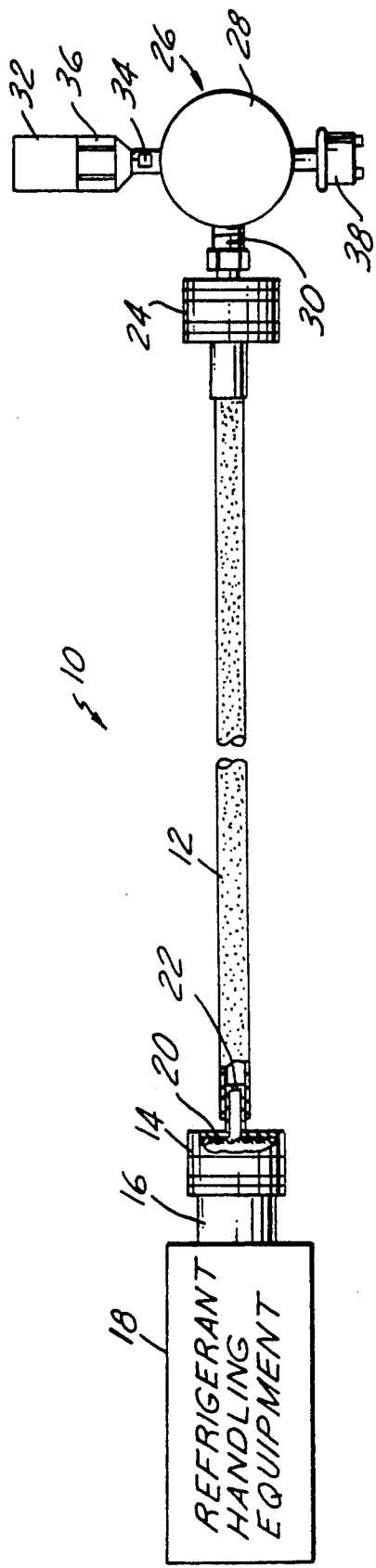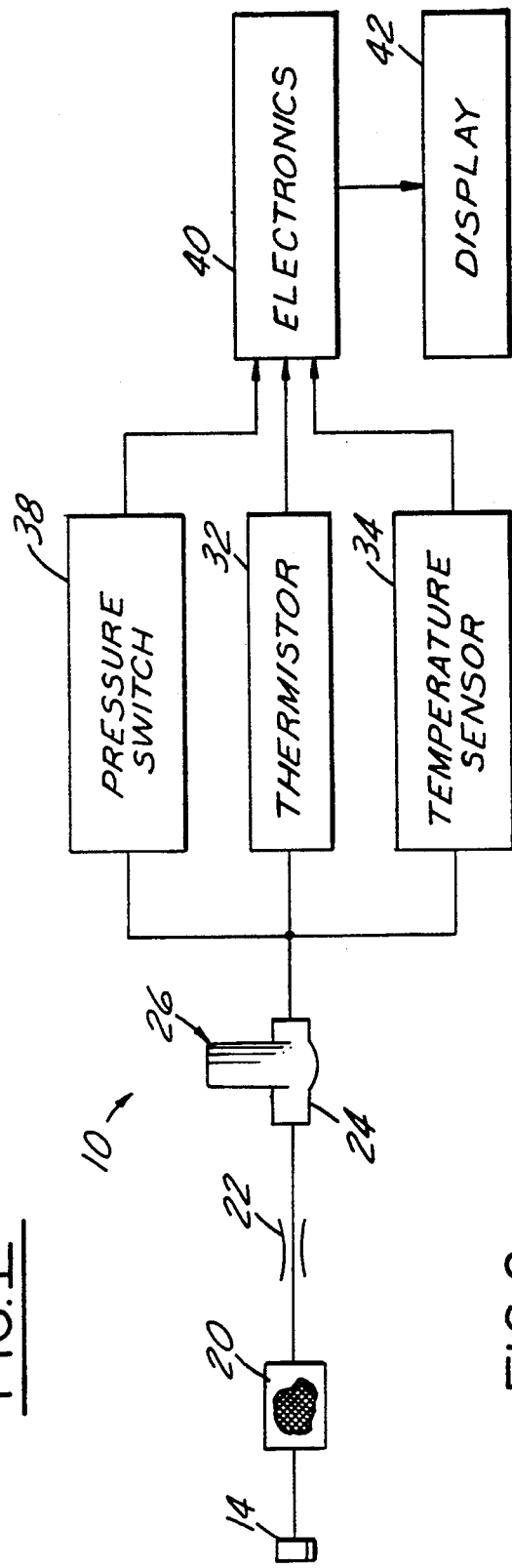

APPARATUS FOR IDENTIFYING AND DISTINGUISHING DIFFERENT REFRIGERANTS

The present invention is directed to refrigerant handling systems such as air conditioners and heat pumps, and more particularly to apparatus for identifying and distinguishing different types of refrigerants for service of such systems Yet more specifically, the present invention relates to improvements in the apparatus disclosed in U.S. Pat. No. 5,158,747.

BACKGROUND AND OBJECTS OF THE INVENTION

It is now widely recognized and accepted that release into the atmosphere of chlorofluorocarbon(CFC)-based refrigerants, such as refrigerant R12, has a deleterious effect upon the ozone layer that surrounds the earth. Production of CFC-based refrigerants may be severely curtailed in the future, and the cost of refrigerant for service purposes is already increasing. It is therefore becoming standard practice in the refrigerant system service industry to recover, purify and reuse refrigerant in a refrigeration system under service, rather than merely to vent such refrigerant into the atmosphere and replace with new refrigerant, as had been common practice in the past. U.S. Pat. Nos. 4,768,347, 4,805,416 and 4,878,356, all assigned to the assignee hereof, disclose equipment for recovering, purifying and/or recharging refrigerant in a refrigeration system service environment.

As currently envisioned, R12 refrigerant will eventually be replaced by different types of refrigerants in production of new refrigeration systems. For example, R12 refrigerant may be replaced by R134a refrigerant in the automotive industry—i.e., in automotive air conditioning systems. However, because these refrigerants and their associated lubricants are chemically incompatible with each other, inadvertent mixture of even small amounts of the different refrigerants can cause severe damage and early failure of the refrigeration system. It has been proposed to provide different service fittings on refrigeration equipment using different types of refrigerants, but the use of adaptors and the like in the service industry may still result in inadvertent mixing of refrigerant/lubricant types, with consequent damage to the system under service or to the service equipment itself.

A further complication arises with the use of intermediate refrigerants as substitutes for R12 refrigerant, such as ternary blends made by DuPont. With severe curtailment of R12 production that may take place, it is anticipated that a significant number of refrigeration systems currently employing R12 refrigerant may eventually be retrofitted with an intermediate substitute refrigerant. Inadvertent mixing of refrigerants is considered to be an irreversible process, leading to disposal of the mixed refrigerant as hazardous waste. U.S. Pat. No. 4,939,905, assigned to the assignee hereof, discloses a refrigerant recovery system that includes a recovery compressor, a multiple-section condenser, and means for automatically distinguishing between R12, R22 and R502 refrigerants at the compressor inlet, as a function of refrigerant vapor pressure and temperature, and switching the compressor outlet among the condenser sections to prevent mixing of refrigerants in the condenser. However, the temperature/saturation pressure characteristics of R12, R134a and blend refrigerants are such that these refrigerants cannot as readily be distinguished as a function of these characteristics.

There is therefore a need in the refrigeration system service industry for a device that can be employed to test refrigerant in a storage container or in a refrigeration system before performing service on the system, that is not restricted to any particular type of refrigerant or to automotive service applications, that is particularly well adapted to identify and distinguish between refrigerants of different types, that is inexpensive to manufacture and market, that is readily portable, that is rapid and efficient in operation, and/or that can be employed by relatively untrained service personnel.

U.S. Pat. No. 5,158,747 discloses such a device for identifying and distinguishing between and among different types of refrigerant. The device includes a fixed volume for containing a sample of refrigerant. The refrigerant to be tested is selectively admitted into the volume in vapor phase, vapor pressure of refrigerant within the fixed volume is measured, and admission of refrigerant into the fixed volume is terminated when the vapor pressure of refrigerant contained therein reaches a preselected level. A sensor and associated electronics are coupled to the sample-containing volume for determining type of refrigerant vapor as a function of one or more selected properties of the refrigerant, and indicating such refrigerant type to an operator.

A general object of the present invention is to provide apparatus for identifying and distinguishing different refrigerants of the type disclosed in the noted patent that is more economical to assembly, easy to use and reliable over an extended useful life.

SUMMARY OF THE INVENTION

Apparatus for identifying and distinguishing between at least two types of refrigerant in accordance with the present invention includes a fixed volume for containing a refrigerant sample at controlled vapor pressure. A thermistor provides a first electrical signal as a function of the combined effect of vapor thermal conductivity and temperature of a refrigerant sample in the sample-containing volume, and a temperature sensor provides a second electrical signal as a function of temperature of the refrigerant vapor in the sample-containing volume essentially independent of thermal conductivity thereof. Associated electronics determines type of refrigerant in the sample-containing volume as a function of the first and second electrical signals, and thus as a function of thermal conductivity of the refrigerant sample independent of sample temperature. Since thermal conductivity of refrigerants at a given temperature and pressure varies for different refrigerant types, refrigerant type can be determined and displayed to an operator.

The sample-containing volume in the preferred embodiments of the invention includes a vapor pressure regulator for maintaining the refrigerant sample at a preselected vapor pressure. The vapor pressure regulator may be of conventional type that maintains refrigerant vapor pressure in the sample-containing volume at the preselected pressure as long as inlet pressure is above such preselected pressure, and maintains refrigerant vapor pressure in the sample-containing volume at inlet pressure when inlet pressure is below the preselected pressure. Most preferably, in such embodiments of the invention, a pressure sensor is operatively coupled to the sample-containing volume for indicating vapor pressure of refrigerant contained therein, and enabling determination of refrigerant type when refrigerant vapor pressure reaches the desired level. The vapor pressure regulator may comprise a pressure relief valve operatively coupled to the sample-containing volume for bleeding refrigerant vapor from the sample-containing volume when pressure therein exceeds the desired level. Alternatively, solenoid valve may also be coupled to the pressure sensor for terminating flow of refrigerant when refrigerant vapor pressure in the sample-containing volume reaches the desired level. In the preferred embodiments of the invention, refrigerant vapor pressure within the sample-containing volume is maintained at a level of substantially 40 psig.

The refrigerant identifying apparatus of the invention may be provided as part of a refrigerant handling system, such as the refrigerant recovery, purification and recharging systems disclosed in above-noted U.S. Pat. Nos. 4,768,347, 4,805,416 and 4,878,356. The system operator may thus determine the type of refrigerant in equipment to be serviced before initiating such service, and adjust the service equipment, select the storage container, etc. accordingly. Alternatively, the apparatus for identifying and distinguishing between refrigerant types in accordance with the present invention may be provided as separate apparatus for releasable connection to the refrigerant handling equipment. In one such embodiment herein disclosed, the apparatus of the present invention includes an inlet hose for flexible interconnection to a refrigerant service fitting of the handling equipment. In another embodiment of the invention, the apparatus takes the form of a gauge constructed to be held in a user's hand and removably coupled to the refrigerant service fitting as in the manner of a tire pressure gauge. Most preferably, the apparatus refrigerant inlet includes an orifice for inhibiting flow of liquid refrigerant to the sample-containing volume, and a screen or other suitable filter for preventing entry of dirt to the sample volume.

BRIEF DESCRIPTION OF THE DRAWINGS

The invention, together with additional objects, features and advantages thereof, will be best understood from the following description, the appended claims and the accompanying drawings in which:

FIG. 1 is a partially schematic diagram of refrigerant vapor sampling and testing apparatus in accordance with one presently preferred embodiment of the invention;

FIG. 2 is a functional block diagram of the apparatus illustrated in FIG. 1;

DETAILED DESCRIPTION OF PREFERRED EMBODIMENTS

Figure 3:
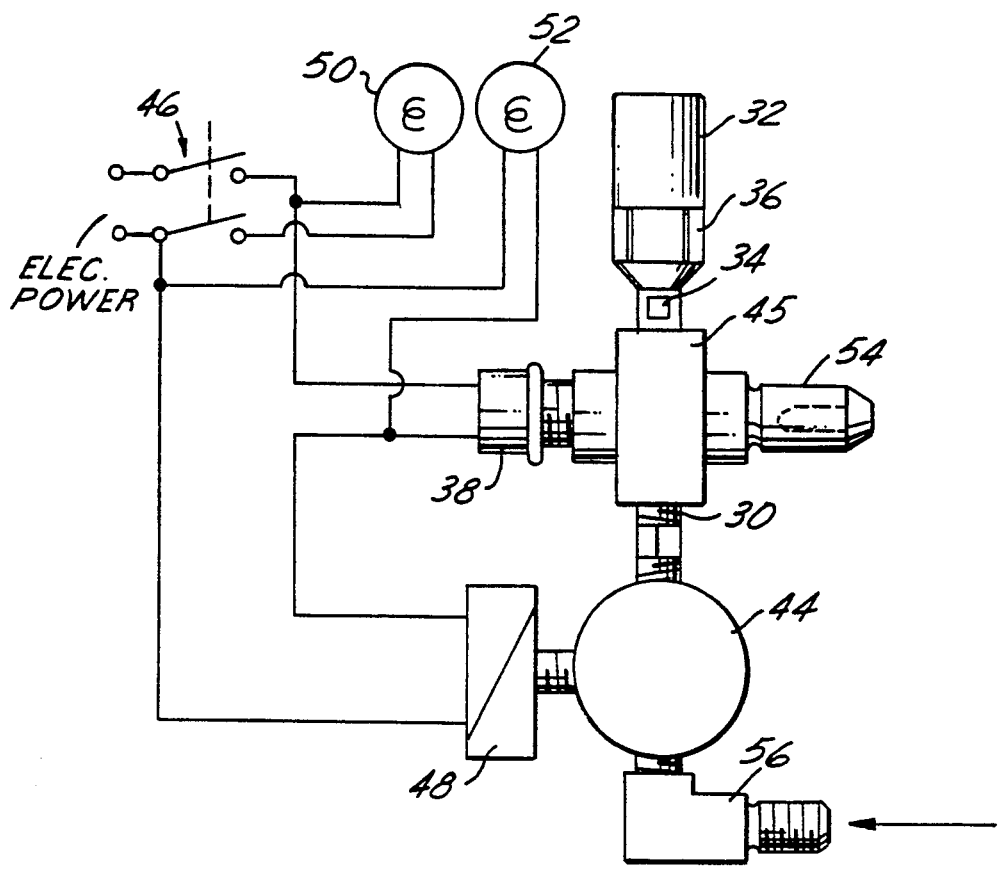
FIG. 3 is a schematic diagram of test apparatus in accordance with a second embodiment of the invention.

The disclosure of U.S. Pat. No. 5,158,747 is incorporated herein by reference.

FIGS. 1 and 2 illustrate apparatus 10 for identifying and distinguishing between and among types of refrigerants in accordance with one presently preferred embodiment of the invention as comprising a flexible hose 12 having a self-sealing quick-disconnect coupling 14 fastened to one end thereof. Coupling 14 preferably is of a type disclosed in U.S. Pat. No. 5,005,375 assigned to the assignee hereof, being adapted for releasable engagement with a service fitting 16 on refrigerant handling (or storage) equipment 18 for which refrigerant type is to be tested. Hose 12 is fitted at or adjacent to coupler 14 with a filter screen 20 for inhibiting entry of dirt with sample refrigerant, and with an orifice 22 for inhibiting entry of liquid refrigerant. A second connector 24 at the opposing end of hose 12 is removably coupled to a test assembly 26.

Test assembly 26 includes a pressure regulator 28 having an inlet fitting 30 coupled to connector 24. A thermistor 32 and a temperature sensor 34 are mounted on a fitting 36 that is coupled to one outlet of pressure regulator 26. A pressure switch 38 is coupled to another outlet of pressure regulator 28 in parallel with thermistor 32 and temperature sensor 34. As shown in FIG. 2, pressure switch 38, thermistor 32 and temperature sensor 34 all provide electrical signals to sensor electronics 40, which identifies and distinguishes refrigerant type based upon such signals as will be described. Electronics 40 drives a display 42 that indicates refrigerant type to an operator. Several exemplary displays are illustrated in above-noted U.S. Pat. No. 5,158,747.

In operation, refrigerant vapor is fed to pressure regulator 28, which in turn regulates outlet refrigerant pressure to a predetermined level when inlet refrigerant pressure is above such level, and to the level of inlet refrigerant vapor pressure when such inlet pressure is below the desired level set at the regulator. Regulator 28 may comprise an R040R-02S05 shop-air type regulator marketed by Numatics Corp., with Neoprene W seals for compatibility with refrigerants. The fixed volume that contains the refrigerant test sample is thus the internal volume of regulator 28 downstream of the regulating mechanism, coupled with the internal volume of fitting 36 on which thermistor 32 and temperature sensor 34 are mounted. Thermistor 32 is, of course, an active sensing element that provides a signal to electronics 40 that varies as a function of both refrigerant temperature within the contained volume and thermal conductivity of contained refrigerant sample. Temperature sensor 34 is a passive sensor that provides a corresponding electrical signal to electronics 40 that varies solely as a function of contained refrigerant temperature, and substantially independently of thermal conductivity.

Thus, electronics 40 may determine thermal conductivity properties of the contained refrigerant sample as a combined function of the thermistor and temperature sensor signals. In effect, the temperature sensor signal is employed to eliminate the temperature effects of the thermistor signal. Since such thermal conductivity properties at a given temperature measured by sensor 34, and at a given pressure set by regulator 28, vary with refrigerant type, refrigerant type is therefore determined by electronics 40 as a function of such thermal conductivity properties and indicated at display 42. Pressure sensor 38 functions to determine that pressure within the sample volume is at the desired level, and signals electronics 40 accordingly. If pressure is at the desired level, a measurement of refrigerant type is enabled. If pressure is below the desired level, display 40 may so indicate to the operator. Regulator 28 includes facility for adjusting pressure of refrigerant within the sample volume, preferably to a level of 40 psig in accordance with the preferred embodiments of the invention. Following a test sequence, coupling 14 may be removed from equipment fitting 16 and coupled to a vacuum pump, which may then be energized to evacuate test apparatus 10 preparatory to further use.

FIG. 3 illustrates a modified embodiment of the invention in which a solenoid valve 44 is connected to inlet 30 of a fitting 45. Utility or battery power is applied by an operator switch 46. Switch 46 is connected through pressure sensor 38 for applying power to the coil 48 of valve 44 and open the valve when pressure within the sample volume is below the desired level, and for closing valve 44 and thereby terminating inlet refrigerant flow when sample vapor pressure reaches the desired level. In this way, the refrigerant vapor sample is brought to and maintained at the desired level within fitting 45. A pair of lamps 50,52 indicate application of electrical power and availability of desired test pressure respectively. A valved fitting 54 is connected to fitting 45 for evacuating the regulator and sample volume following completion of a test sequence. Hose connector 24 (FIG. 1) is connected to fitting 56 of valve 44, and the embodiment of FIG. 3 otherwise operates in the manner set forth above in connection with FIGS. 1 and 2.

Figure 4:
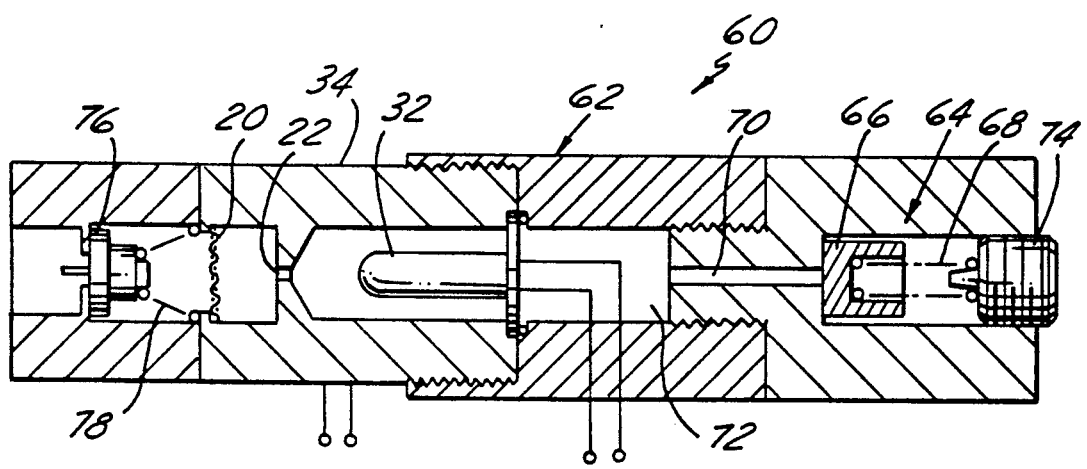
FIG. 4 is a sectional view of test apparatus in accordance with a third embodiment of the invention.

FIG. 4 illustrates a hand-held embodiment 60 of the present invention in which a multi-piece housing 62 contains screen 20, orifice 22, temperature sensor 34 and thermistor 32. A pressure relief valve 64 is mounted at one end of housing 62, including a valve element 66 adjustably biased by a coil spring 68 to close a bleed passage 70 that opens into the fixed sample volume 72. Pressure applied by spring 68 is adjustable by means of a threaded plug 74. A check valve 76 is disposed at the opposing end of housing 62, and is biased to a closed position by a coil spring 78. When housing 62 is fitted over refrigerant service fitting 16 (FIG. 1), the valve within the service fitting opens check valve 76 against the force of coil spring 78 to admit refrigerant to volume 72 through screen 20 and orifice 22. When the pressure of refrigerant within the test sample volume reaches the desired level adjustably determined by plug 74, refrigerant bleeds through passage 70 so that pressure relief valve 64 maintains the test refrigerant sample at the desired pressure. After completion of a test sequence, housing 62 may be hand held over the inlet fitting of a vacuum pump to open check valve 76 and evacuate volume 72. Orifice 22 may be in the range of 0.014 to 0.035 inches. Valve 64 may be a type B-4CPA2-3 valve sold by NuPro.

We claim:

1. Apparatus for identifying and distinguishing between at least two types of refrigerant comprising:
   means for containing a refrigerant sample at controlled vapor pressure,
   first means for providing a first electrical signal as a function of combined effect of thermal conductivity and temperature of a refrigerant sample in said sample-containing means,
   second means for providing a second electrical signal as a function of temperature of the refrigerant sample in said sample-containing means, and
   means for indicating type of refrigerant in said containing means as a function of said first and second signals.

2. The apparatus set forth in claim 1 wherein said sample-containing means comprises means for maintaining the refrigerant sample in said containing means at a preselected vapor pressure.

3. The apparatus set forth in claim 2 wherein said means for maintaining vapor pressure comprises a pressure regulator that maintains refrigerant vapor pressure in said sample-containing means at said preselected pressure as long as inlet pressure is above said preselected pressure, and that maintains refrigerant vapor pressure in said sample-containing means at inlet pressure when inlet pressure is below said preselected pressure.

4. The apparatus set forth in claim 3 further comprising pressure sensing means operatively coupled to said sample-containing means for indicating vapor pressure of refrigerant in said sample-containing means.

5. The apparatus set forth in claim 4 wherein said pressure sensing means is coupled to said type-indicating means for enabling indication of refrigerant type responsive to said first and second signals when refrigerant vapor pressure in said sample-containing means reaches said preselected pressure.

6. The apparatus set forth in claim 2 wherein said means for maintaining vapor pressure comprises pressure sensing means operatively coupled to said sample-containing means and a solenoid valve responsive to said pressure sensing means for terminating flow of refrigerant to said sample-containing means when refrigerant vapor pressure in said sample-containing means reaches said preselected pressure.

7. The apparatus set forth in claim 2 wherein said vapor pressure regulating means comprises a pressure relief valve operatively coupled to said sample-containing means for bleeding refrigerant vapor from said sample-containing means when pressure exceeds said preselected pressure.

8. The apparatus set forth in claim 2 wherein said preselected pressure is 40 psig.

9. The apparatus set forth in claim 1 further comprising inlet means for feeding a refrigerant sample to said sample-containing means.

10. The apparatus set forth in claim 9 wherein said inlet means comprises an orifice for inhibiting flow of liquid refrigerant to said sample-containing means.

11. The apparatus set forth in claim 10 wherein said inlet means further comprises a filter screen for preventing flow of dirt to said sample-containing means.

12. The apparatus set forth in claim 9 wherein said inlet means includes means for engagement with a refrigerant fitting to admit a refrigerant sample, and a check valve for preventing reverse flow of refrigerant from said inlet means upon disengagement from such fitting.

13. The apparatus set forth in claim 9 wherein said inlet means includes a hose flexibly coupling said filtering-engagement means with said sample-containing means.

* * * * *